US009265409B2

(12) United States Patent
Ishihara

(10) Patent No.: US 9,265,409 B2
(45) Date of Patent: Feb. 23, 2016

(54) CAPSULE MEDICAL DEVICE AND CAPSULE MEDICAL SYSTEM

(75) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1034 days.

(21) Appl. No.: 12/599,737

(22) PCT Filed: May 20, 2008

(86) PCT No.: PCT/JP2008/059211
§ 371 (c)(1),
(2), (4) Date: Nov. 11, 2009

(87) PCT Pub. No.: WO2008/143246
PCT Pub. Date: Nov. 27, 2008

(65) Prior Publication Data
US 2010/0210903 A1    Aug. 19, 2010

(30) Foreign Application Priority Data

May 22, 2007 (JP) ................................. 2007-135805

(51) Int. Cl.
*A61B 1/04* (2006.01)
*A61B 1/00* (2006.01)
*A61B 5/00* (2006.01)
*A61B 5/07* (2006.01)
*A61B 5/06* (2006.01)

(52) U.S. Cl.
CPC ............. *A61B 1/041* (2013.01); *A61B 1/00004* (2013.01); *A61B 1/043* (2013.01); *A61B 5/0071* (2013.01); *A61B 5/0084* (2013.01); *A61B 5/073* (2013.01); *A61B 1/00036* (2013.01); *A61B 5/0075* (2013.01); *A61B 5/065* (2013.01)

(58) Field of Classification Search
CPC ................................ A61B 1/041; A61B 1/043
See application file for complete search history.

(56) References Cited

U.S. PATENT DOCUMENTS

| 5,749,830 | A | 5/1998 | Kaneko et al. | |
|---|---|---|---|---|
| 6,240,312 | B1 * | 5/2001 | Alfano et al. | 600/476 |
| 2002/0085753 | A1 | 7/2002 | Sendai | |
| 2003/0117491 | A1 | 6/2003 | Avni et al. | |
| 2004/0143157 | A1 | 7/2004 | Doguchi et al. | |
| 2004/0189798 | A1 * | 9/2004 | Hakamata | 348/65 |
| 2004/0257438 | A1 | 12/2004 | Doguchi et al. | |
| 2005/0027166 | A1 | 2/2005 | Matsumoto et al. | |

(Continued)

FOREIGN PATENT DOCUMENTS

| EP | 1 099 405 A1 | 5/2001 |
|---|---|---|
| JP | 7-222712 | 8/1995 |

(Continued)

OTHER PUBLICATIONS

International Search Report dated Aug. 19, 2008.

*Primary Examiner* — Anhtuan T Nguyen
*Assistant Examiner* — Alexandra Newton
(74) *Attorney, Agent, or Firm* — Scully, Scott, Murphy & Presser, PC

(57) ABSTRACT

Radiation is captured without fail, and a sharp image of a region where radiation is generated is acquired. A capsule medical device (3) includes an excitation light source (7) that generates excitation light for irradiating an inner wall (4) of a body cavity, a CCD (9), having variable sensitivity, that captures fluorescence generated at the inner wall (4) of the body cavity by the excitation light emitted from the excitation light source (7) to acquire a two-dimensional fluorescence image, and a control unit (35) that performs control so as to reduce the sensitivity of the CCD (9) when the fluorescence intensity in at least part of the fluorescence image acquired by the CCD (9) exceeds a predetermined threshold.

8 Claims, 18 Drawing Sheets

(56) References Cited

U.S. PATENT DOCUMENTS

2005/0154227 A1* 7/2005 Stroefer et al. ............... 560/345
2006/0209185 A1* 9/2006 Yokoi ............................. 348/65

FOREIGN PATENT DOCUMENTS

| | | |
|---|---|---|
| JP | 2002-233492 | 8/2002 |
| JP | 2003-102672 A | 4/2003 |
| JP | 2004-024496 | 1/2004 |
| JP | 2004-535878 A | 12/2004 |
| JP | 2005-13279 | 1/2005 |
| JP | 2006-25802 | 2/2006 |
| JP | 2006-61399 A | 3/2006 |
| JP | 2006-524097 A | 10/2006 |
| WO | WO 03/009739 A2 | 2/2003 |
| WO | WO 2004/082472 A1 | 9/2004 |

* cited by examiner

BINNING IN EACH DIRECTION

BINNING DISABLED

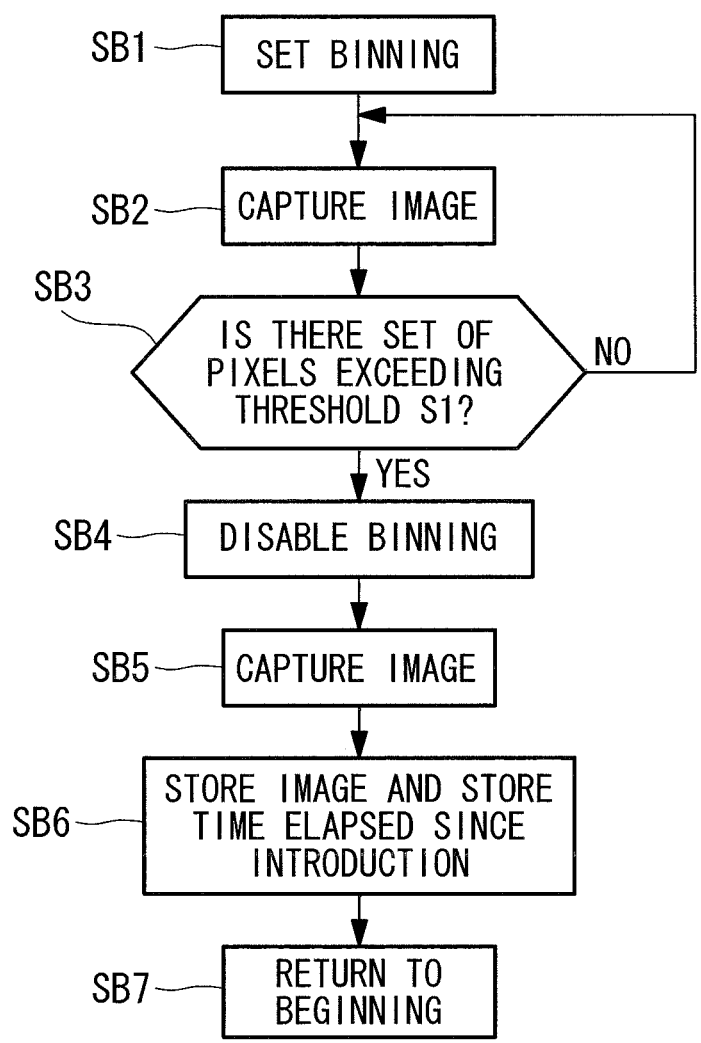

ALL PIXELS ARE BINNED TOGETHER

BINNING DISABLED

CAPSULE MEDICAL DEVICE AND CAPSULE MEDICAL SYSTEM

TECHNICAL FIELD

The present invention relates to capsule medical devices and capsule medical systems.

BACKGROUND ART

Hitherto, there have been known endoscope devices with which a fluorescent material having affinity for diseased tissue, such as cancer, is introduced in advance into the body of a subject under examination, and excitation light that excites the fluorescent material is radiated to detect fluorescence from the fluorescent material accumulated in diseased tissue (see Patent Document 1).

According to Patent Document 1, a plurality of fluorescence wavelengths in a near infrared wavelength region is detected by a wired endoscope device, and functions equivalent to those of the wired endoscope device are employed in a wireless capsule endoscope by using a plurality of light-emitting elements with different wavelengths, such as LEDs.

Usually, a capsule endoscope is swallowed through the mouth of a subject for inspection, and then sequentially captures images while moving in the body cavity by means of peristalsis until it is naturally evacuated. While the capsule endoscope moves in the body cavity, image data captured in the body by the capsule endoscope is transmitted to the outside by wireless communication or the like and is stored in a memory provided outside. Then, after the capsule endoscope is evacuated, images of organs based on the image data stored in the memory are displayed on the display to perform diagnosis.

Patent Document 1:
Japanese Unexamined Patent Application, Publication No. 2006-25802

DISCLOSURE OF INVENTION

With the capsule endoscope according to Patent Document 1, images are consecutively captured and stored at predetermined time intervals from introduction into the subject to evacuation, for example, during a period of approximately 8 hours. Thus, a large number of useless images having no light intensity exist in a huge number of stored images, so that a long time is needed to check all the images.

On the other hand, when the sensitivity of an image-capturing element is increased in order to detect radiation radiated from diseased tissue, for example, very weak fluorescence from a fluorescent material accumulated in diseased tissue, an image having low resolution is acquired or a shaky image is acquired, resulting in degradation of the image quality.

The present invention provides a capsule medical device and a capsule medical system with which it is possible to capture radiation without fail and to acquire a sharp image of a region where radiation is generated.

A first aspect of the present invention is a capsule medical device including an excitation light source that generates excitation light for irradiating an inner wall of a body cavity; an image-capturing element that captures radiation generated at the inner wall of the body cavity by the excitation light emitted from the excitation light source to acquire a two-dimensional radiation image and that has variable sensitivity; and control means for performing control so as to reduce the sensitivity of the image-capturing element when the radiation intensity in at least part of the radiation image acquired by the image-capturing element exceeds a predetermined threshold.

According to this aspect, the body cavity wall is irradiated with the excitation light emitted from the excitation light source, and radiation generated in the body cavity wall is captured by the operation of the image-capturing element to acquire a two-dimensional radiation image. In this case, first, an image is captured with a high sensitivity of the image-capturing element, and then an image is captured with a reduced sensitivity. By capturing an image with a high sensitivity of the image-capturing element, it is possible to capture radiation generated in the body cavity wall without fail, for example, weak radiation radiated from diseased tissue, such as weak fluorescence from a fluorescent material accumulated in diseased tissue.

Furthermore, by the operation of the control means, the sensitivity of the image-capturing element is reduced when the radiation intensity in at least part of the radiation image acquired by the image-capturing element exceeds the predetermined threshold, so that it is possible to improve the image quality of the acquired image. Accordingly, it is possible to acquire a sharp image of a site of the inner wall of the body cavity having a region where the radiation intensity exceeds the predetermined threshold.

Therefore, it is possible to reduce the possibility of failure to detect a diseased region and to capture a sharp image representing the shape and size of the diseased region, as well as the presence or absence thereof. Furthermore, by saving only images captured with a reduced sensitivity, it is possible to save the labor of checking a huge number of images including images not having regions with high luminance levels and to observe diseased regions efficiently and in detail.

In the first aspect described above, the control means may be configured to reduce the number of pixels processed together by binning of the image-capturing element when the radiation intensity in at least part of the radiation image acquired by the image-capturing element exceeds the predetermined threshold.

With this configuration, by increasing the number of pixels processed together by binning of the image-capturing element, at the expense of resolution, the total radiation detected by a large number of pixels is captured, so that it is possible to readily detect the presence or absence of radiation. Furthermore, at a site where radiation exists, by reducing the number of pixels processed together by binning of the image-capturing element, it is possible to increase resolution, thereby acquiring a sharp image of the vicinity of the site.

Alternatively, in the first aspect described above, the control means may be configured to reduce the exposure time of the image-capturing element when the radiation intensity in at least part of the radiation image acquired by the image-capturing element exceeds the predetermined threshold.

With this configuration, by extending the exposure time of the image-capturing element, at the expense of the frame rate, radiation is detected with an increased amount of light, so that it is possible to readily detect the presence or absence of radiation. Furthermore, at a site where radiation exists, by reducing the exposure time of the image-capturing element, it is possible to increase the frame rate and to alleviate the effect of shaking, thereby acquiring a sharp image of the vicinity of the site.

Alternatively, in the first aspect described above, there may be further provided a diaphragm having an aperture whose size is variable to adjust the amount of radiation that enters the image-capturing element, and the control means may be configured to reduce the size of the aperture of the diaphragm when the radiation intensity in at least part of the radiation image acquired by the image-capturing element exceeds the predetermined threshold.

With this configuration, by increasing the size of the aperture of the diaphragm, at the expense of the depth of field, radiation is detected with an increased amount of light, so that it is readily possible to detect the presence or absence of radiation. Furthermore, at a site where radiation exists, by reducing the size of the aperture of the diaphragm, it is possible to increase the depth of field, thereby acquiring a sharp image of the vicinity of the site.

Furthermore, in the first aspect, the radiation may be fluorescence or Raman scattered light generated at the inner wall of the body cavity.

Furthermore, in the first aspect, there may be further provided a timer that measures time and storage means for storing an image captured with reduced sensitivity of the image-capturing element, in association with the time measured by the timer.

With this configuration, it is possible to store in the storage means a sharp image of a region where the radiation intensity exceeds the predetermined threshold in association with time. Therefore, it is possible to estimate a position where the image was captured on the basis of the movement time of the capsule medical device, so that it becomes possible to detect the location of a diseased region.

A second aspect of the present invention is a capsule medical system comprising a capsule medical device according to the first aspect described above and an extracorporeal device disposed outside the body of a patient, wherein the capsule medical device includes transmitting means for transmitting image signals of an image acquired by the image-capturing element to the outside, and wherein the extracorporeal device includes receiving means for receiving the image signals from the transmitting means; a timer that measures time; and storage means for storing the image signals received by the receiving means, in association with the time measured by the timer.

According to this aspect, by the operation of the transmitting means of the capsule medical device, image signals of a sharp image of a region where the radiation intensity exceeds the predetermined threshold is transmitted to the receiving means and is received by the receiving means of the extracorporeal device. At the extracorporeal device, time measured by the timer and the image signals received by the receiving means are stored in the storage means in association with each other. Accordingly, it is possible to estimate the position where the image was captured on the basis of the movement time of the capsule medical device, so that it becomes possible to detect the location of a diseased region.

According to the present invention, there is an advantage that it is possible to capture radiation without fail and to acquire a sharp image of a region where radiation is generated.

BRIEF DESCRIPTION OF DRAWINGS

FIG. 8 is a flowchart showing the operation of the capsule medical system in FIG. 6.

EXPLANATION OF REFERENCE SIGNS

2: Patient
3: Capsule medical device
4: Inner wall of body cavity
7: Excitation light source
9: CCD (image-capturing element)
35: Control unit (control means)

Best Mode For Carrying Out The Invention (First Embodiment)

Hereinafter, a capsule medical system according to a first embodiment of the present invention will be described with reference to the drawings.

Figure 1:
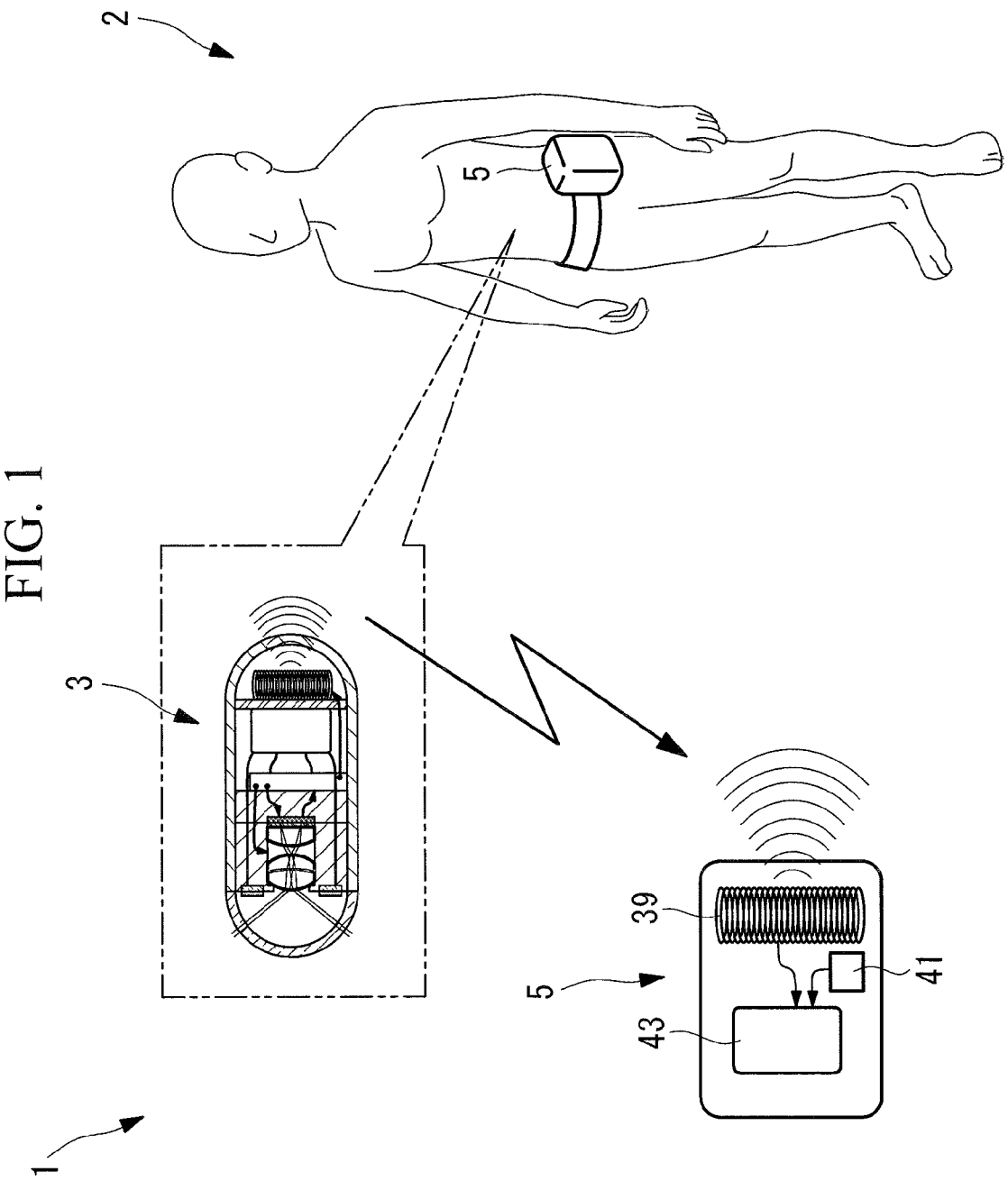
FIG. 1 is a schematic diagram showing a capsule medical system according to a first embodiment of the present invention.

As shown in FIG. 1, a capsule medical system 1 according to this embodiment includes a capsule medical device 3 that is introduced into the body of a patient 2 to capture images of the inner wall of the body cavity and to output the captured image data to the outside, and includes an extracorporeal device 5 that receives the image data signals output from the capsule medical device 3 and that saves the image data.

Figure 2:
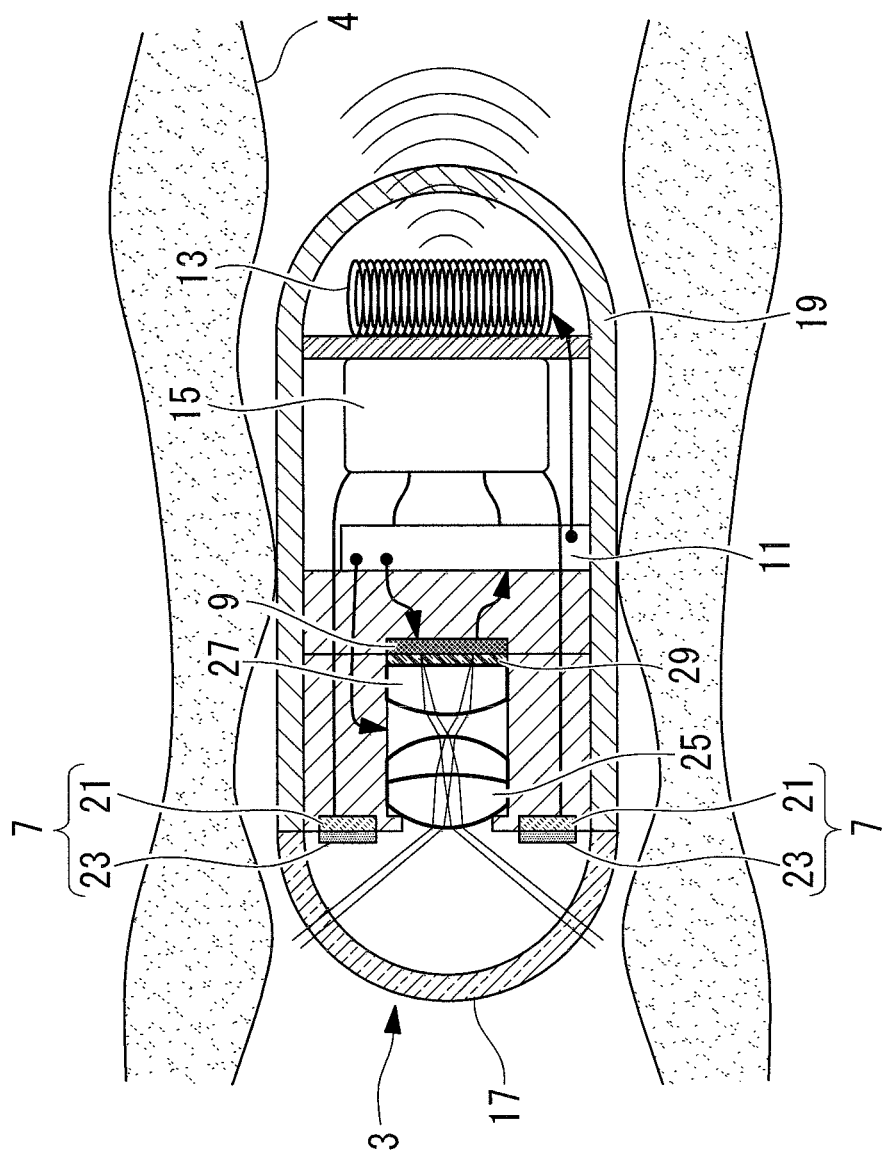
FIG. 2 is a diagram showing a capsule medical device in FIG. 1.

As shown in FIG. 2, the capsule medical device 3 is a capsule endoscope of a direct viewing type. Inside a capsule case 19 formed in the shape of a capsule, the capsule medical device 3 includes excitation light sources 7 that generate excitation light for irradiating the inner wall 4 of the body cavity therewith, a CCD (image-capturing element) 9 that captures fluorescence (radiation) generated at the inner wall 4 of the body cavity by the excitation light generated from the excitation light sources 7 and that generates electrical signals corresponding to the individual fluorescence luminance levels of two-dimensionally arrayed pixels, a control device 11 that generates fluorescence image information based on the electrical signals acquired by the CCD 9 and that controls the sensitivity of the CCD 9, a transmitting antenna (transmitting means) 13 that transmits the fluorescence image information acquired by the CCD 9 to the outside, and a battery 15 that supplies electric power to the excitation light sources 7, the control device 11, and the transmitting antenna 13.

Furthermore, the capsule case 19 has a transparent window 17 on one end in the lengthwise direction thereof. The irradiation with excitation light and detection of fluorescence are performed through the transparent window 17.

The plurality of excitation light sources 7 are provided with gaps along the circumferential direction of the capsule body and are arranged so that excitation light is emitted through the transparent window 17. Furthermore, each of the excitation light sources 7 has an LED 21 and an excitation filter 23 that transmits excitation light having predetermined wavelengths in the light emitted from the LED 21. Thus, excitation light emitted from the plurality of the LEDs 21 and transmitted through the individual excitation filters 23 is transmitted through the transparent window 17 and irradiates the inner wall 4 of the body cavity of the patient 2.

The CCD 9 is provided substantially at the center of the capsule case 19 so that light entering the capsule case 19 through the transparent window 17 is captured therewith. In front of the CCD 9, a light collecting lens 25 that collects light entering through the transparent window 17 and an image forming lens 27 that forms an image with light collected by the light collecting lens 25 are provided. Furthermore, upstream of the CCD 9, an excitation-light cutting filter 29 that cuts light having wavelengths other than predetermined wavelengths, i.e., fluorescence wavelengths, is provided. The CCD 9 is thus configured to convert fluorescence generated at the inner wall 4 of the body cavity and transmitted through the light collecting lens 25, the image forming lens 27, and the excitation-light cutting filter 29 into electrical signals for individual pixels. Furthermore, the CCD 9 is configured to output the generated electrical signals to the control device 11.

Figure 3:
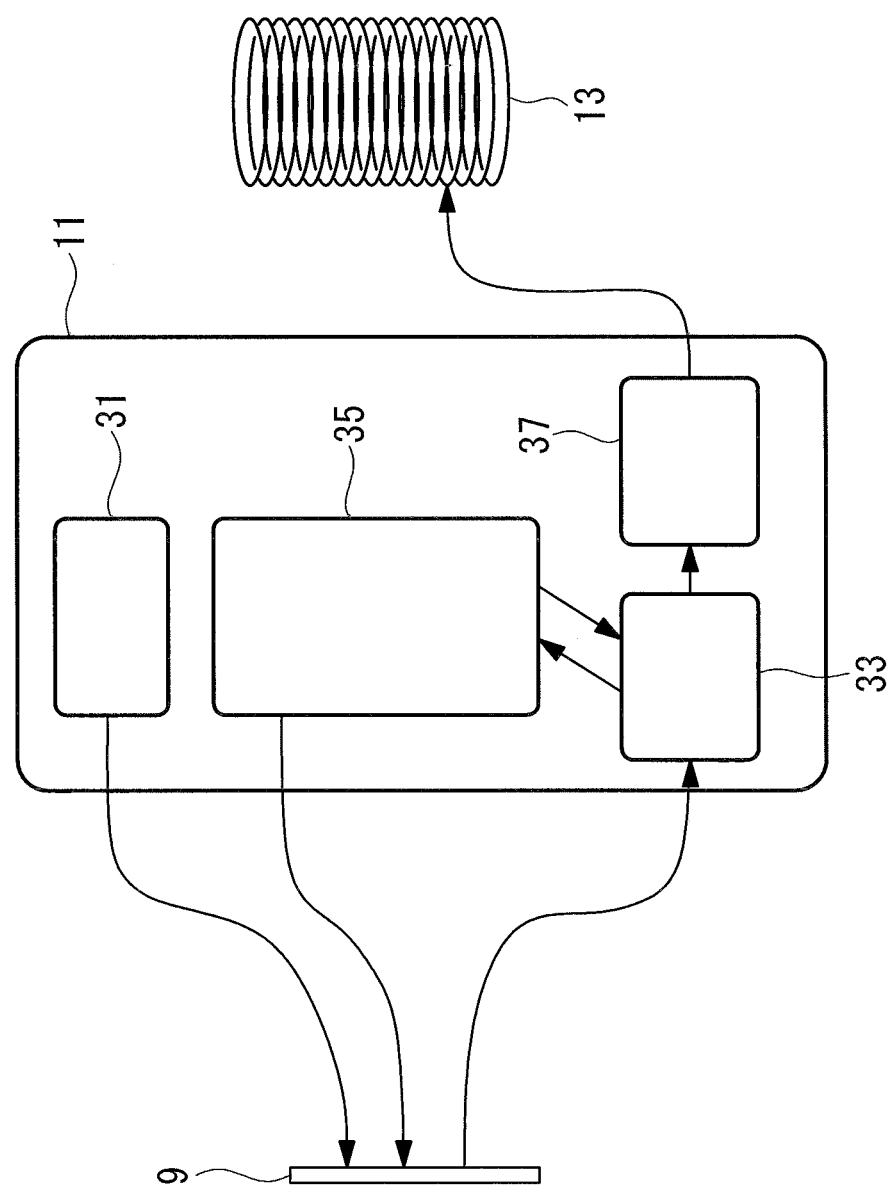
FIG. 3 is a diagram showing a control device and a transmitting antenna in FIG. 1.

As shown in FIG. 3, the control device 11 includes an image-capturing-element driving unit 31 that drives the CCD 9, a signal reading unit 33 that reads the electrical signals from the CCD 9, a control unit (control means) 35 that controls the sensitivity of the CCD 9 on the basis of the electrical signals read by the signal reading unit 33, and an image-information constructing unit 37 that constructs fluorescence image information on the basis of the electrical signals from the signal reading unit 33.

The control unit 35 is configured to control the sensitivity of the CCD 9, i.e., to control a binning setting. Furthermore, when the binning setting of the CCD 9 is disabled, the control unit 35 is configured to control the signal reading unit 33 so that electrical signals acquired by the CCD 9 with the binning setting thereof disabled are output to the image-information constructing unit 37. The image-information constructing unit 37 is thus configured to receive the electrical signals from the signal reading unit 33 and to construct fluorescence image information. Furthermore, the image-information constructing unit 37 is configured to output the constructed fluorescence image information to the transmitting antenna 13.

Upon receiving the input fluorescence image information from the image-information constructing unit 37, the transmitting antenna 13 is configured to output the fluorescence image information to the extracorporeal device 5.

As shown in FIG. 1, the extracorporeal device 5 is configured so that it can be attached to, for example, the patient 2 with the capsule medical device 3 introduced in the body thereof. The extracorporeal device 5 includes a receiving antenna (receiving means) 39 that receives the fluorescence image information transmitted from the transmitting antenna 13 of the capsule medical device 3, a timer 41 that measures the time elapsed from introduction to evacuation of the capsule medical device 3 into and from the body of the patient 2, and a memory (storage means) 43 that stores the fluorescence image information received by the receiving antenna 39 in association with the time measured by the timer 41.

The operation of the thus-configured capsule medical device 1 according to this embodiment will be described with reference to FIGS. 4A to 4C and FIG. 5.

Figure 4A:
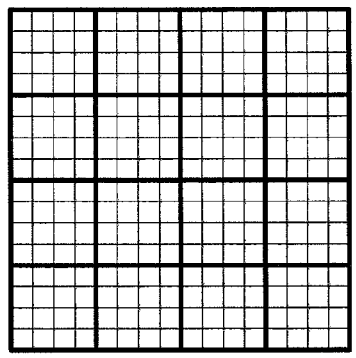
FIG. 4A is a diagram showing a state where the binning setting of a CCD in FIG. 1 is set to 4×4.

First, the extracorporeal device 5 is attached to the patient 2, and the capsule medical device 3 is set to initial setting. Specifically, the operation of the image-capturing-element driving unit 31 is started, and the binning setting of the CCD 9 is set to binning by 4×4 (step SA1), as shown in FIG. 4A. Then, the timer 41 of the extracorporeal device 5 is started and the capsule medical device 3 is introduced into the body of the patient 2.

When the capsule medical device 3 is introduced into the body of the patient 2, excitation light emitted from the excitation light sources 7 is radiated onto the inner wall 4 of the body cavity of the patient 2 through the transparent window 17. If any diseased tissue exists on the inner wall 4 of the body cavity irradiated with the excitation light, fluorescence is emitted from a fluorescent material accumulated in the diseased tissue. The fluorescence generated at the inner wall 4 of the body cavity enters the capsule medical device 3 through the transparent window 17 thereof, is transmitted through the light collecting lens 25, the image forming lens 27, and the excitation-light cutting filter 29, and is then captured by the CCD 9 (step SA2). At the CCD 9, the fluorescent light formed into an image by the image forming lens 27 is converted into electrical signals.

In this case, since the binning setting of the CCD 9 is set to binning by 4×4, electrical signals of a set of pixels composed of 4×4=16 pixels are summed, and the sum is acquired as an electrical signal of one pixel. Therefore, even if fluorescence detected at each pixel is weak, the electrical signal based on the set of pixels, representing the sum for 16 pixels, is relatively intense and is detected without fail, so that the presence or absence of fluorescence can be readily detected.

The electrical signals acquired by the CCD 9 are output to the control device 11 and read by the signal reading unit 33, and it is determined by the operation of the control unit 35 whether there exists a set of pixels exceeding a predetermined threshold S1 (step SA3). If it is determined as a result that there exists no set of pixels exceeding the threshold S1, the procedure returns to step SA2 ("NO" in step SA3), and the operation of steps SA2 and SA3 is repeated until a set of pixels exceeding the threshold S1 is found.

Figure 4B:
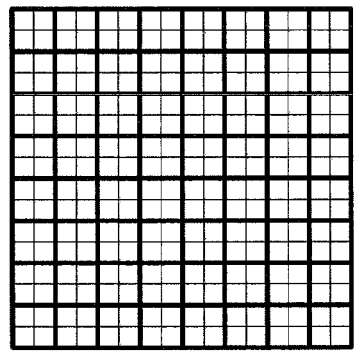
FIG. 4B is a diagram showing a state where the binning setting of the CCD in FIG. 1 is set to 2×2.

On the other hand, if it is determined that there exists a set of pixels exceeding the threshold S1 ("YES" in step SA3), the control unit 35 sets the binning setting of the CCD 9 to binning by 2×2 (step SA4), as shown in FIG. 4B. Then, an image of a site of the inner wall 4 of the body cavity substantially the same as the site captured in step SA2 is captured by operation of the CCD 9 set to binning by 2×2 (step SA5).

In this case, since the CCD 9 is set to binning by 2×2, a sum of electrical signals for a set of pixels composed of 2×2=4 pixels is acquired. Thus, it is possible to reduce the sensitivity and increase the resolution, so that it is possible to acquire a sharper image, compared with the previous image, of the vicinity of the site where fluorescence exists.

The electrical signals from sets of pixels, acquired by the CCD 9 set to binning by 2×2, are read by the signal reading unit 33 of the control device 11, and it is determined by the operation of the control unit 35 whether there exists a set of pixels exceeding a predetermined threshold S2 (step SA6).

If it is determined that there exists no set of pixels exceeding the threshold S2 ("NO" in step SA6), the procedure returns to step SA1 by the operation of the control unit 35, and the binning setting of the CCD 9 is set to binning by 4×4, which is the same as the initial setting. Then, the operation of steps SA1 to SA6 is repeated until a set of pixels exceeding the threshold S2 is found.

Figure 4C:
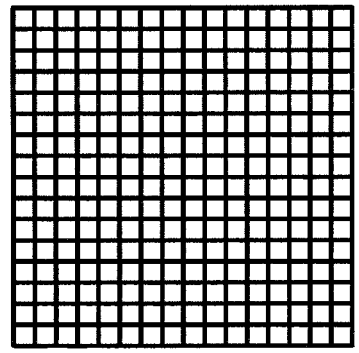
FIG. 4C is a diagram showing a state where the binning setting of the CCD in FIG. 1 is disabled.
Figure 5:
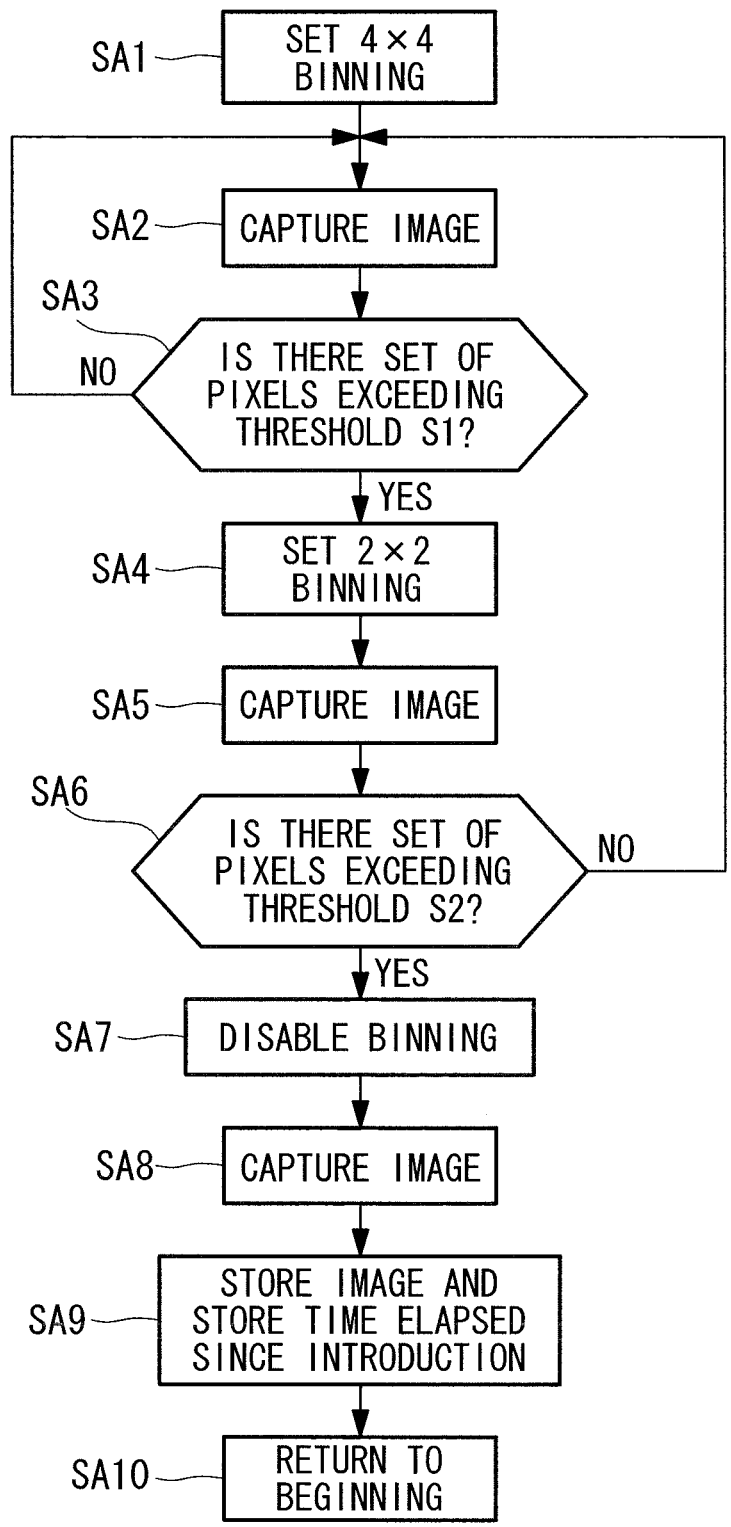
FIG. 5 is a flowchart showing the operation of the capsule medical system in FIG. 1.

On the other hand, if it is determined that there exists a set of pixels exceeding the threshold S2 ("YES" in step SA6), the control unit 35 disables the binning setting of the CCD 9 (step SA7), as shown in FIG. 4C. Then, an image of a site of the inner wall 4 of the body cavity substantially the same as the site captured in step SA5 is captured (step SA8).

In this case, since the binning setting is disabled, electrical signals are acquired on a per-pixel basis. Therefore, an image can be acquired at maximum resolution. Accordingly, a shaper image of the inner wall 4 of the body cavity having a region where the fluorescence intensity exceeds the threshold S2 can be acquired.

The electrical signals acquired by the CCD 9 at this time are output from the signal reading unit 33 to the image-information constructing unit 37 by the operation of the control unit 35, where fluorescence image information is constructed. The fluorescence image information constructed by the image-information constructing unit 37 is output to the transmitting antenna 13 and is transmitted from the transmitting antenna 13 to the receiving antenna 39 of the extracorporeal device 5.

At the extracorporeal device 5, the fluorescence image information received by the receiving antenna 39 is stored in the memory 43 in association with the time measured by the timer 41 (step SA9). Thus, it becomes possible to estimate the position where an image stored in the memory 43 was captured on the basis of the time elapsed from the introduction of the capsule medical device 3 into the body of the patient 2.

When the image capturing described above is performed by the CCD 9 with the binning setting disabled, the procedure returns to step SA1 by the operation of the control unit 35 (step SA10), and the operation of steps SA1 to SA10 is repeated until the capsule medical device 3 is evacuated from the body of the patient 2.

As described above, with the capsule medical system 1 according to this embodiment, images are captured while controlling binning of the CCD 9. Thus, it is possible to reduce the possibility of failure to detect a diseased region, and it is also possible to capture a sharp image representing the shape and size of the diseased region, as well as the presence or absence thereof. Furthermore, since an acquired image is associated with elapsed time, it is possible to detect the location of a diseased region. Furthermore, since only images acquired with the CCD 9 set to a high resolution are transmitted, it is possible to avoid consumption of electrical power for needless transmission of fluorescence image information. Furthermore, since only images acquired with the CCD 9 set to a high resolution are saved, it is possible to save the labor of checking a huge number of images including images not having regions with high luminance levels. As a result, it becomes possible to observe diseased regions efficiently and in detail.

This embodiment can be modified as follows.

Figure 6:
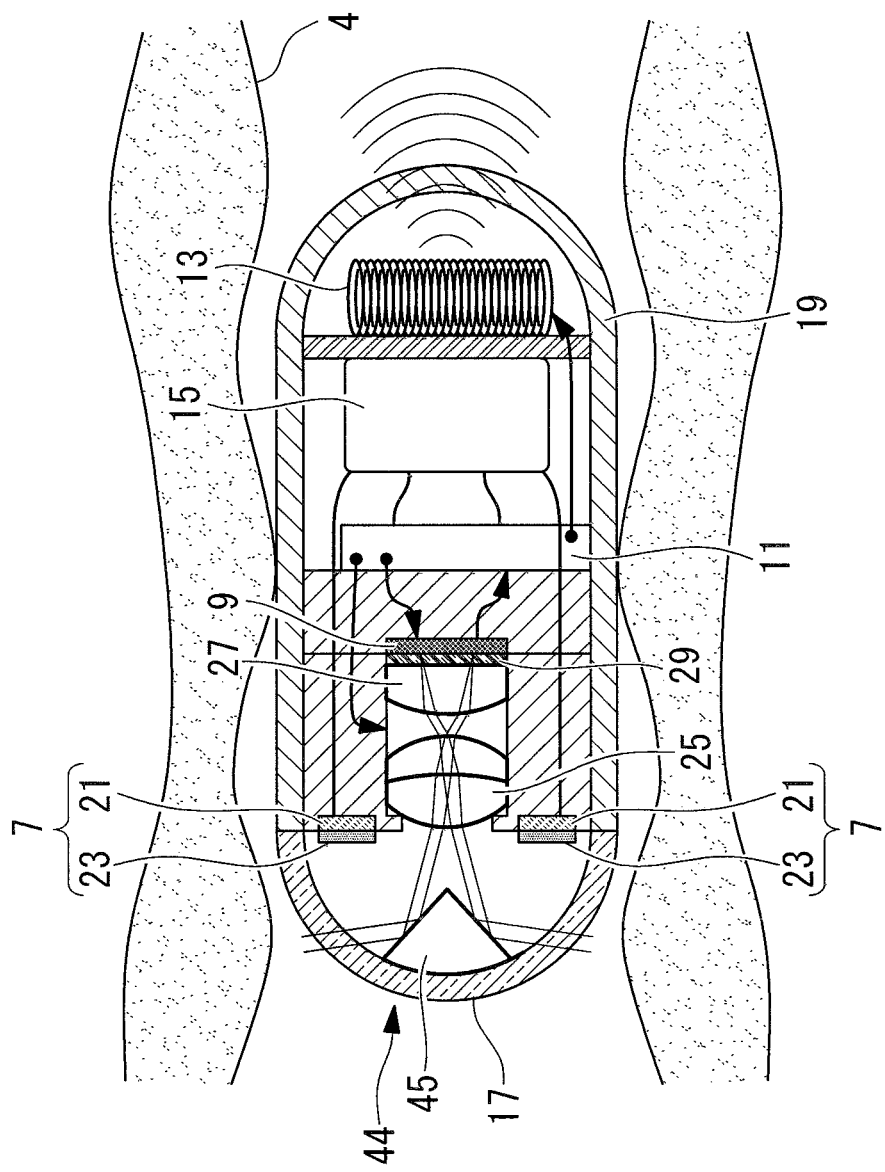
FIG. 6 is a schematic diagram showing a capsule medical device of a capsule medical system according to a modification of the first embodiment of the present invention.

For example, as shown in FIG. 6, a conical mirror 45 may be provided substantially at the center of the transparent window 17 so as to project toward the CCD 9, making a capsule medical device 44 of a side view type. Accordingly, fluorescence generated at the inner wall 4 of the body cavity is reflected by the conical mirror 45 toward the CCD 9, so that fluorescence can efficiently enter the CCD 9 from the outside in radial directions of the capsule medical device 44. Thus, it is possible to capture an image at an angle close to a direction perpendicular to the inner wall 4 of the body cavity, thereby acquiring a sharper image.

Figure 7A:
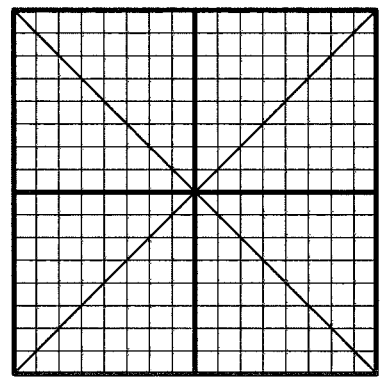
FIG. 7A is a diagram showing a state where the binning setting of a CCD in FIG. 5 is set radially.
Figure 7B:
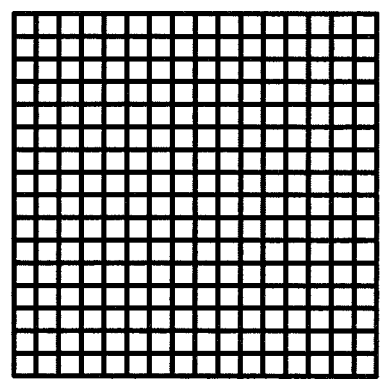
FIG. 7B is a diagram showing a state where the binning setting of the CCD in FIG. 5 is disabled.

As initial setting of the CCD 9, the binning setting may be defined radially, as shown in FIG. 7A. In this case, as shown in FIG. 8, first, binning of the CCD 9 is set radially (step SB1). The CCD 9 captures an image of the inner wall 4 of the body cavity (step SB2), and it is determined by the operation of the control unit 35 whether there exists a set of pixels exceeding the predetermined threshold S1 (step SB3). If it is determined as a result that there exists no set of pixels exceeding the threshold S1, the procedure returns to step SB2. On the other hand, if it is determined that there exists a set of pixels exceeding the threshold S1, the binning setting of the CCD 9 is disabled (step SB4), as shown in FIG. 7B. With the CCD 9 having the binning setting disabled, an image of a site of the inner wall 4 of the body cavity substantially the same as the site captured in step SB2 is captured (step SB5), and fluorescence image information constructed on the basis of the acquired electrical signals is stored in association with time (step SB6). After the image capturing described above is performed by the CCD 9 with the binning setting disabled, the procedure returns to the operation of step SB1 (step SB7), and observation of the inner wall 4 of the body cavity is continued.

Accordingly, since the binning setting is defined radially as the initial setting of the CCD 9, when a set of pixels exceeding the threshold S1 is discovered, it is possible to facilitate recognition of a direction toward fluorescence with respect to a circumferential direction of the capsule case 19.

Figure 9:
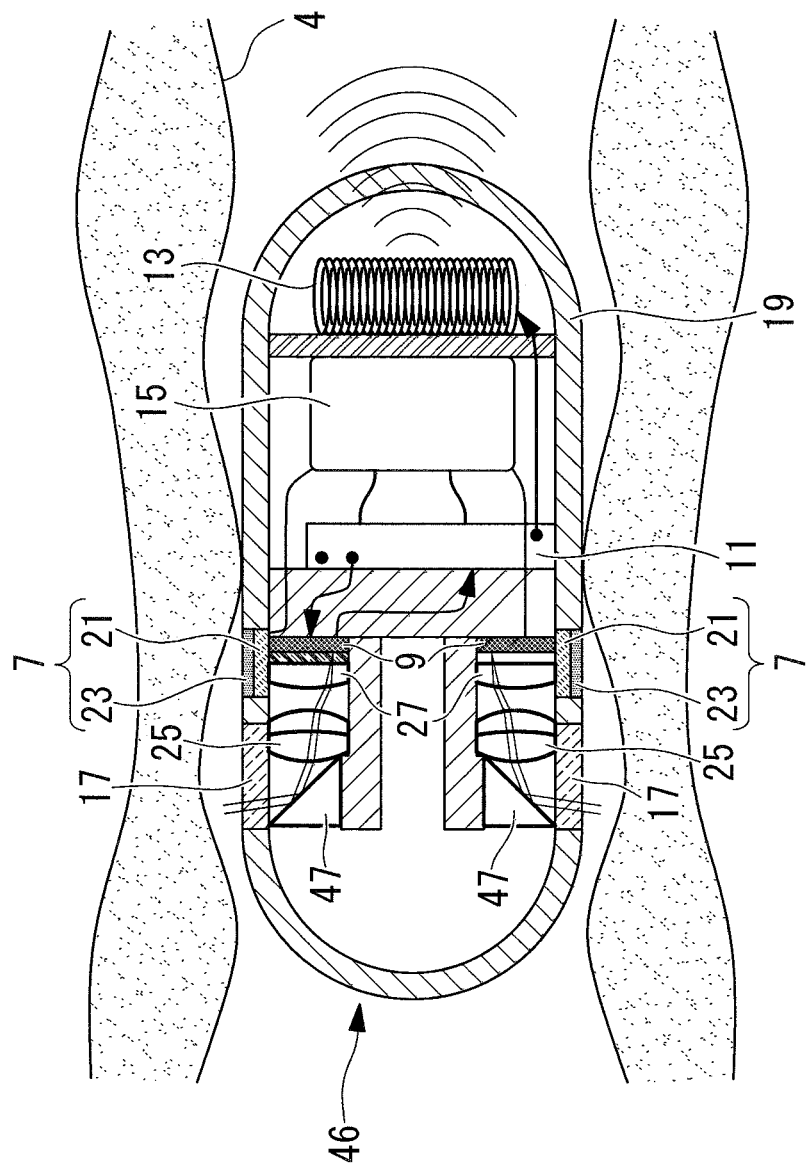
FIG. 9 is a schematic diagram showing a capsule medical device of a capsule medical system according to another modification of the first embodiment of the present invention.
Figure 10:
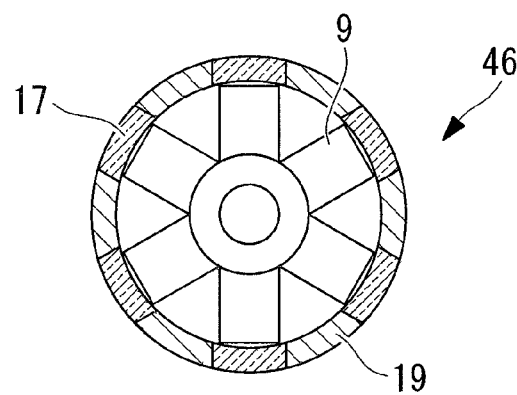
FIG. 10 is a sectional view of the capsule medical device of the capsule medical system according to the other modification of the first embodiment of the present invention.

Alternatively, for example, as shown in FIGS. 9 and 10, excitation light sources 7 may be provided at six positions at regular intervals along the circumferential direction of the capsule case 19, with light collecting lenses 25, image forming lenses 27, excitation-light cutting filters 29, and CCDs 9 provided correspondingly at six positions along the circumferential direction of the capsule body. In this case, portions of the capsule case 19 in the vicinities of the individual light collecting lenses 25 have transparent windows 17 formed therein, and reflecting mirrors 47 are provided in front of the light collecting lenses 25 so that excitation light enters the CCDs 9 from the outside in the radial directions of a capsule medical device 46.

Figure 11A:
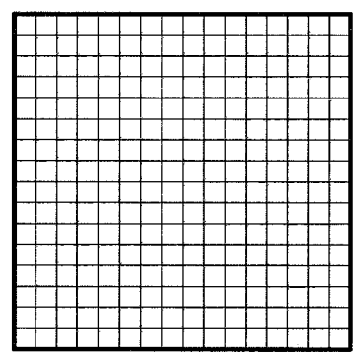
FIG. 11A is a diagram showing a state where the binning setting of a CCD in FIG. 9 is set to bin all the pixels together.
Figure 12:
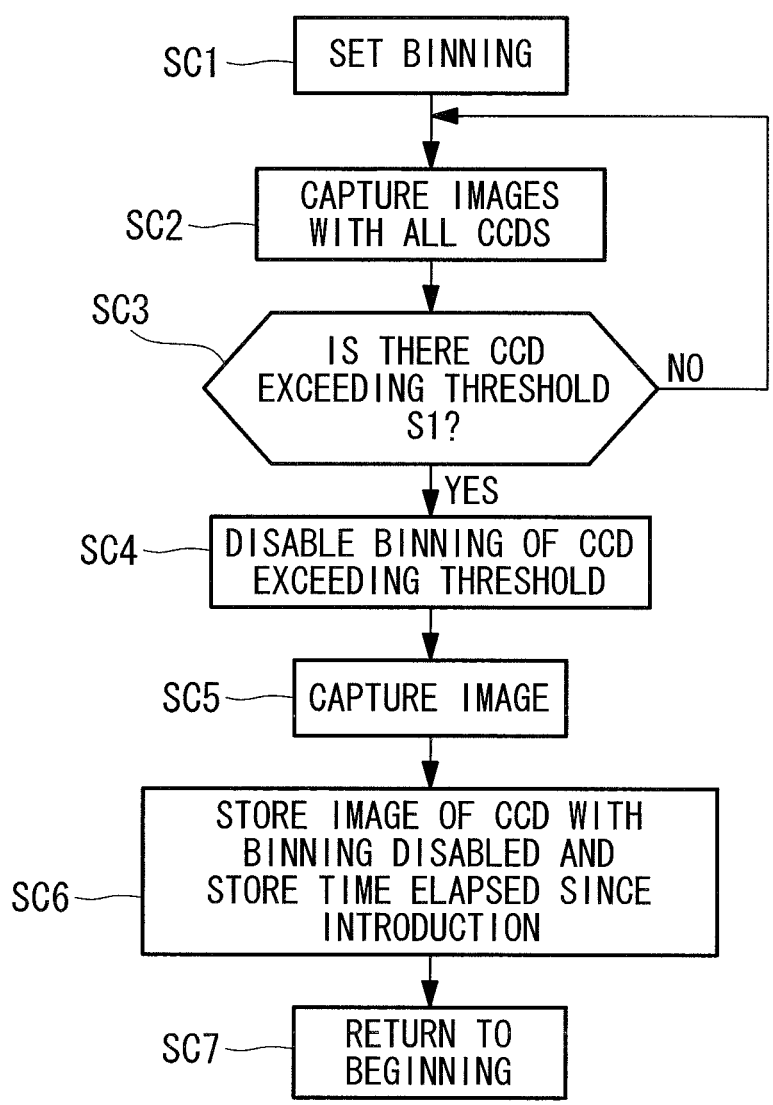
FIG. 12 is a flowchart showing the operation of the capsule medical system in FIG. 9.

In this case, as shown in FIGS. 11A and 12, all the pixels are binned together as the initial setting of the CCDs 9 (step SC1). Thus, at each of the CCDs 9, electrical signals of all the pixels (16×16=256 pixels in the example shown in FIG. 11A) are summed, and the sum is acquired as an electrical signal of one pixel. Accordingly, it is possible to detect fluorescence with maximum sensitivity by causing the capsule medical device 46 to operate as if PDs (photodiodes) were disposed at six positions.

Figure 11B:
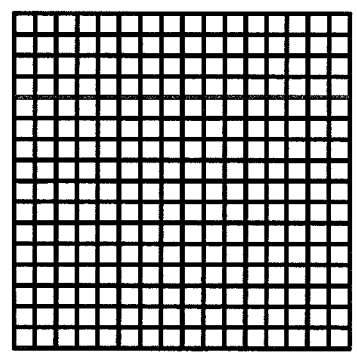
FIG. 11B is a diagram showing a state where the binning setting of the CCD in FIG. 9 is disabled.

Then, images of the inner wall 4 of the body cavity are captured by the CCDs 9 disposed at the six positions (step SC2), and it is determined by the operation of the control unit 35 whether there exists a set of pixels exceeding the predetermined threshold S1 (step SC3). If it is determined as a result that there exists no set of pixels exceeding the threshold S1, the procedure returns to step SC2. On the other hand, if it is determined that there exists a set of pixels exceeding the threshold S1, the binning setting of only the CCD 9 associated with the set of pixels exceeding the threshold S1 is disabled (step SC4), as shown in FIG. 11B. Then, an image is captured by the CCD 9 with the binning setting disabled (step SC5), and fluorescence image information constructed on the basis of the acquired electrical signals is stored in association with time (step SC6). Then, the procedure returns to the operation of step SC1 (step SC7), and observation of the inner wall 4 of the body cavity is continued.

Accordingly, since fluorescence is detected with maximum sensitivity by causing the capsule medical device 46 to operate as if PDs were provided at six positions, it is possible to detect fluorescence without fail. Furthermore, since fluorescence is detected to capture an image by one of the CCDs 9 disposed at six positions along the circumferential direction of the capsule case 19, it is possible to facilitate recognition of a direction toward fluorescence with respect to a circumferential direction of the capsule medical device 46. Furthermore, it is possible to acquire valid fluorescence image information by operating only a CCD 9 that captures an image of a site of the inner wall 4 of the body cavity where fluorescence exists.

Although the excitation light sources 7, the light collecting lenses 25, the image forming lenses 27, the excitation-light cutting filters 29, and the CCDs 9 are provided at six positions in this modification, alternatively, these components may be provided, for example, at two positions or four positions.

[Second Embodiment]

Figure 13:
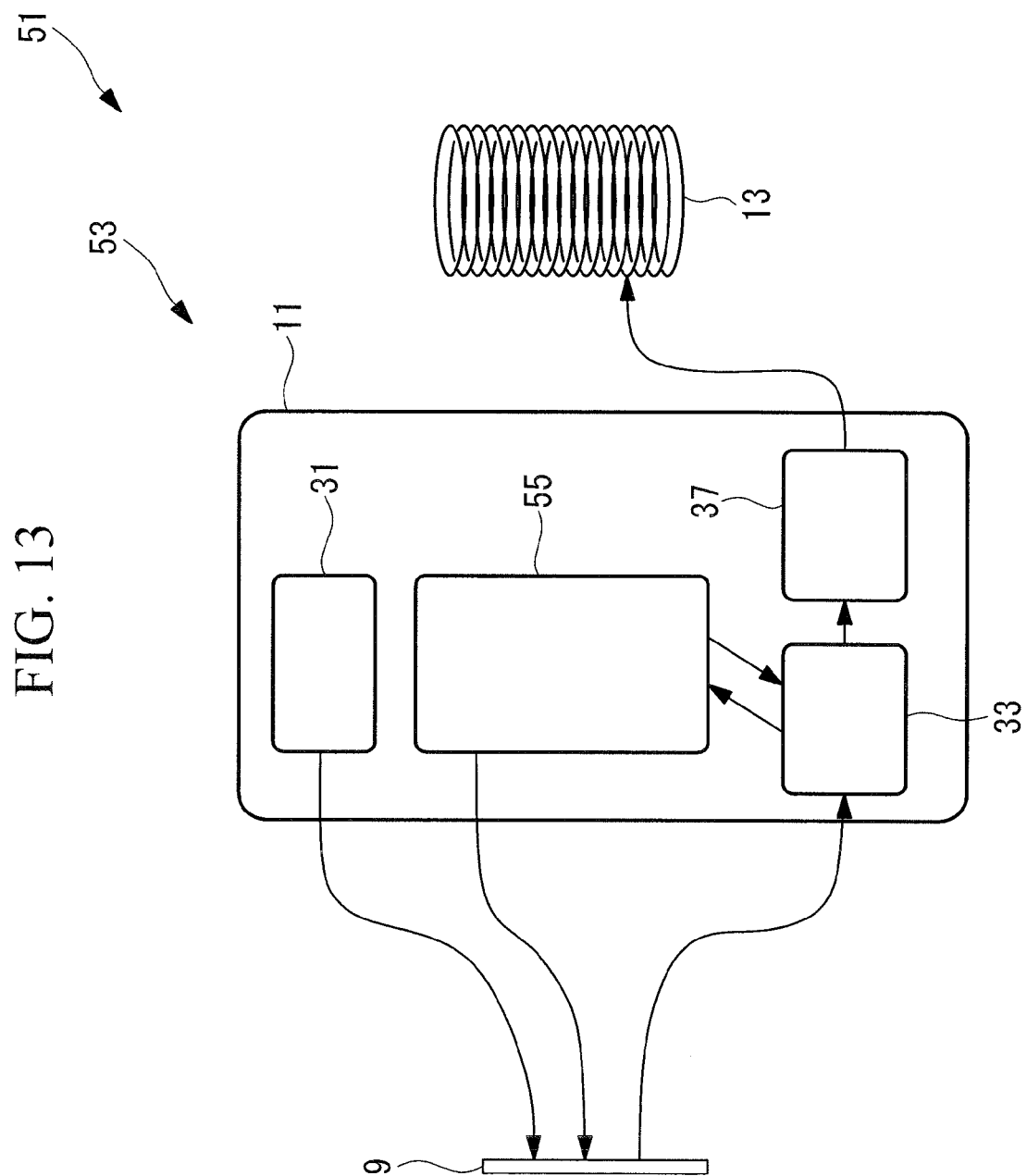
FIG. 13 is a schematic diagram showing a control device and a transmitting antenna of a capsule medical system according to a second embodiment of the present invention.
Figure 14:
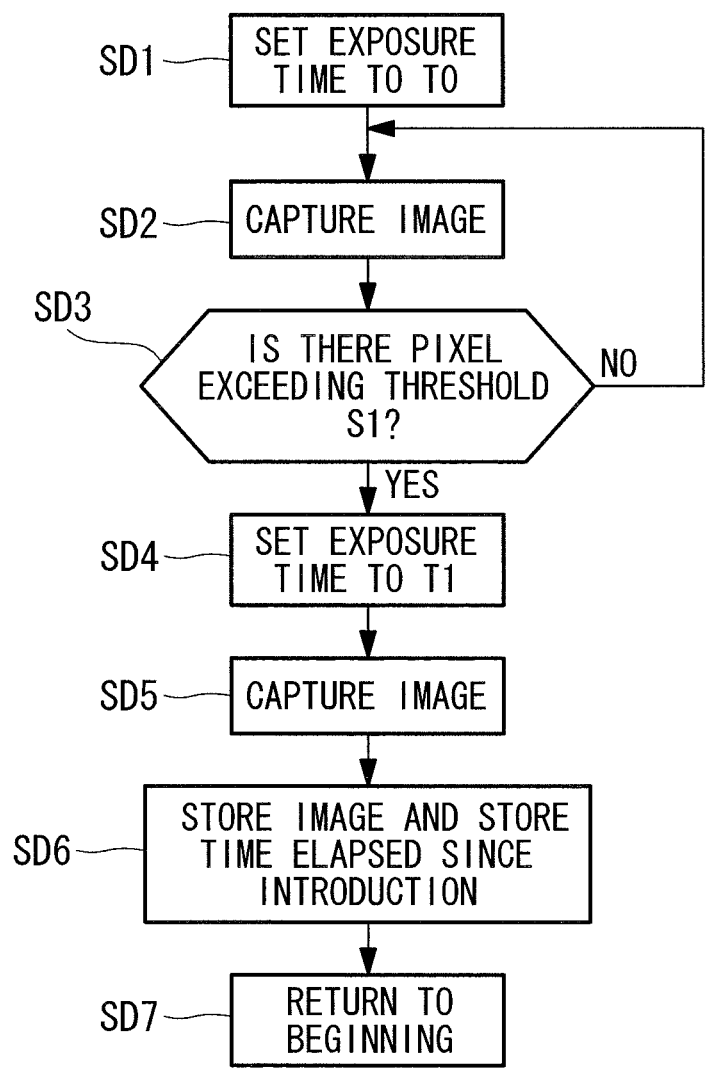
FIG. 14 is a flowchart showing the operation of the capsule medical system in FIG. 13.

Next, a capsule medical system 51 according to a second embodiment of the present invention will be described with reference to FIGS. 13 and 14.

The capsule medical device 51 according to this embodiment differs from the first embodiment in that a control unit 55 of a capsule medical device 53 controls the exposure time of the CCD 9 instead of controlling the binning setting in the first embodiment.

In the following description of this embodiment, parts configured the same as those of the capsule medical system 1 according to the first embodiment will be designated by the same reference signs, and descriptions thereof will be omitted.

The control unit 55 is configured to perform switching of the exposure time of the CCD 9 between an exposure time T1 in which an appropriate amount of light is captured and an exposure time T0 that is longer than the exposure time T1. Furthermore, the control unit 55 is configured to control the signal reading unit 33 so that electrical signals that have been read are output to the image-information constructing unit 37 when the exposure time is set to the exposure time T1.

First, as the initial setting of the capsule medical device 53, the exposure time of the CCD 9 is set to T0 (step SD1). Upon introduction of the capsule medical device 53 into the body of the patient 2, an image is captured by detecting fluorescence at each pixel of the CCD 9 (step SD2). In this case, since the exposure time of the CCD 9 is set to T0 so that the exposure time is long, it is possible to increase the amount of light captured at each pixel compared with the appropriate amount at the expense of the frame rate. Therefore, even with weak fluorescence, since the electrical signal acquired at each pixel becomes relatively intense, it is possible to readily detect the presence or absence of fluorescence without fail.

Then, when it is determined by the operation of the control unit 55 that there exists no pixel exceeding the predetermined threshold S1, the procedure returns to step SD2 ("NO" in step SD3), and the operation of steps SD2 and SD3 is repeated until a pixel exceeding the threshold S1 is found.

On the other hand, when it is determined that there exists a pixel exceeding the threshold S1 ("YES" in step SD3), the control unit 55 sets the exposure time of the CCD 9 to the exposure time T1 (step SD4). Then, an image of a site of the inner wall 4 of the body cavity substantially the same as the site captured in step SD2 is captured in the exposure time T1 (step SD5). In this case, since the exposure time of the CCD 9 is set to the exposure time T1, in which an appropriate amount of light is captured, it is possible to increase the frame rate and to alleviate the effect of shaking, so that it is possible to acquire a sharper image, compared with the previous image, of the vicinity of the site where fluorescence exists.

At the extracorporeal device 5, fluorescence image information constructed on the basis of the electrical signals acquired by the CCD 9 set to the exposure time T1 is stored in the memory 43 in association with time measured by the timer 41 (step SD6). After the image capturing described above is performed by the CCD 9 set to the exposure time T1, the procedure returns to step SD1 by the operation of the control unit 55 (step SD7), and the operation of steps SD1 to SD7 is repeated until the capsule medical device 53 is evacuated from the body of the patient 2.

As described above, with the capsule medical system 51 according to this embodiment, since images are captured while controlling the exposure time of the CCD 9, it is possible to reduce the possibility of failure to detect a diseased region and to capture a sharp image representing the shape and size of the diseased region, as well as the presence or absence thereof. Furthermore, since an acquired image is associated with elapsed time, it is possible to detect the location of a diseased region. Furthermore, since only images captured at an increased frame rate of the CCD 9 and with the effect of shaking alleviated are transmitted, it is possible to avoid consumption of electrical power for needless transmission of fluorescence image information. Furthermore, since only images having regions with high luminance levels are saved, it is possible to save the labor of checking a huge number of images including images not having regions with high luminance levels. Accordingly, it becomes possible to observe diseased regions efficiently and in detail.

This embodiment can be modified as follows.

Figure 18:
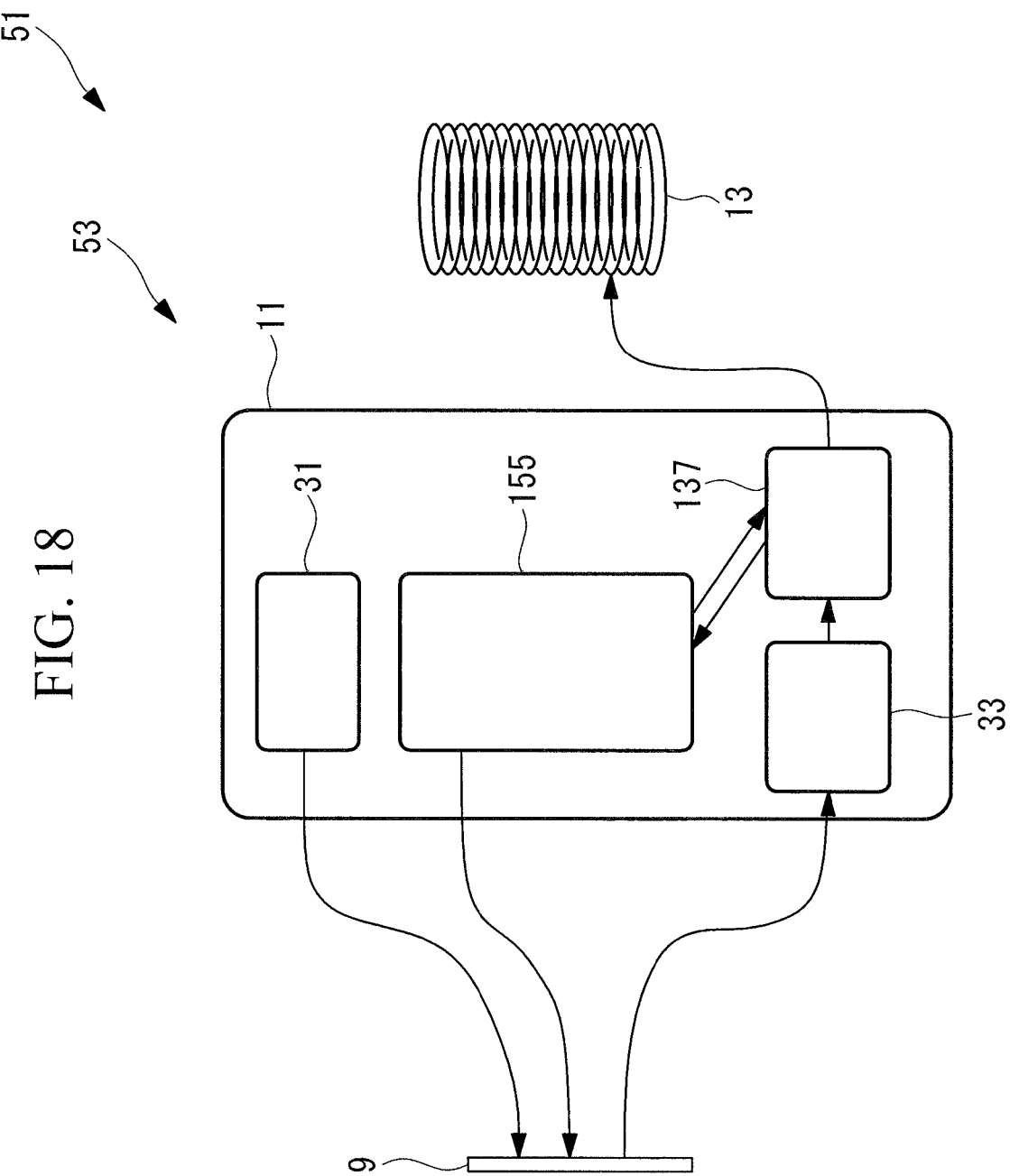
FIG. 18 is a schematic diagram showing a control device and a transmitting antenna of a capsule medical system according to a modification of the second embodiment of the present invention.

In this embodiment, the control unit 55 controls the exposure time of the CCD 9 so that the exposure time is reduced when a region with a high fluorescence luminance level exists, thereby acquiring sharp fluorescence image information. Alternatively, a control unit 155 may be configured to change the number of iterations for an averaging process. For example, as shown in FIG. 18, an image-information constructing unit 137 constructs fluorescence image information consecutively and performs a process of averaging the fluorescence image information constructed a plurality of times, and the control unit 155 reduces the number of iterations for averaging when a region with a high fluorescence luminance level exists.

Figure 19:
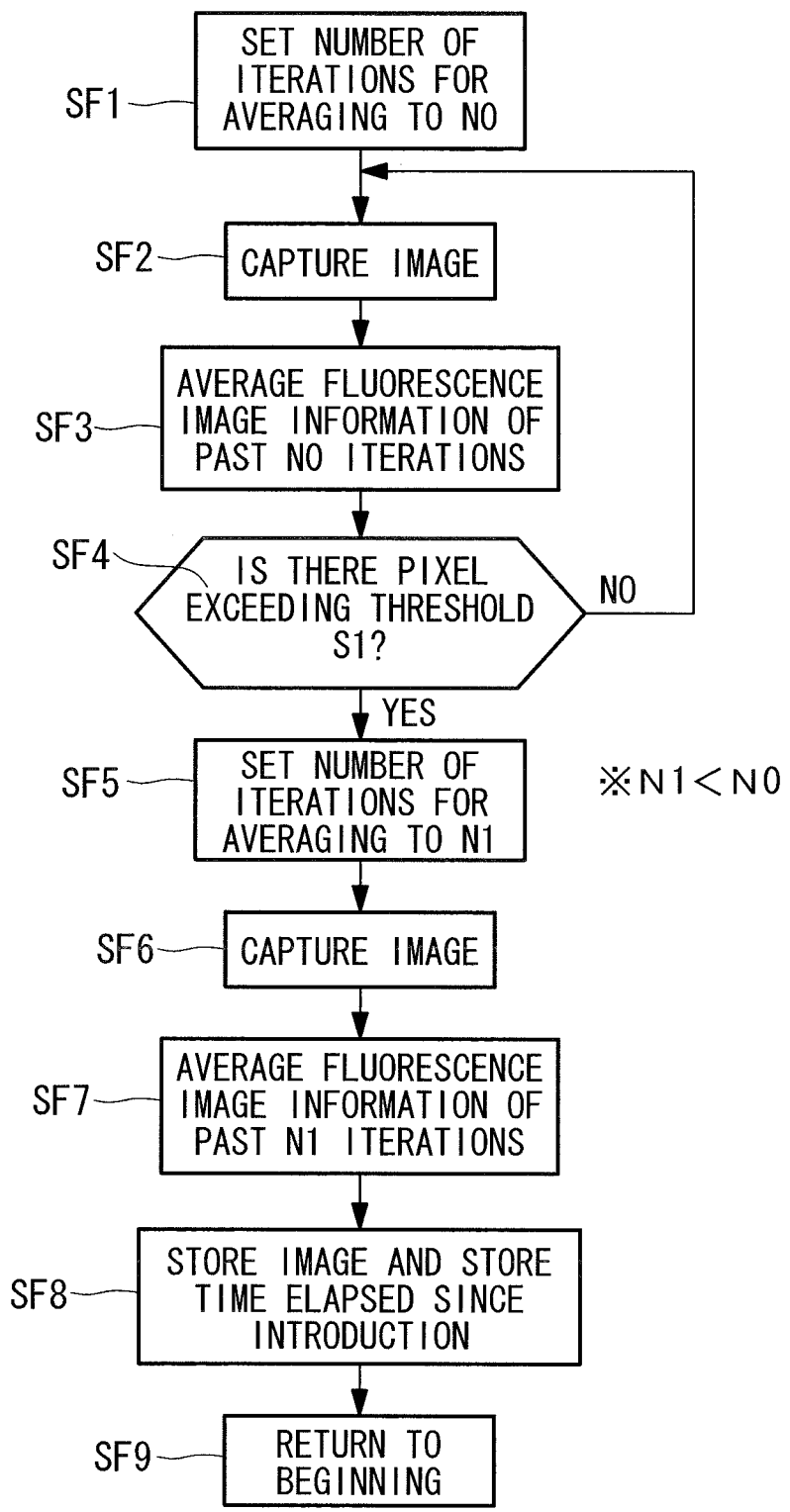
FIG. 19 is a flowchart showing the operation of the capsule medical system in FIG. 18.

Specifically, as shown in FIG. 19, a number of iterations N0 for averaging, representing a large number of construction iterations, is set as the initial setting (step SF1). An image is captured by detecting fluorescence at each pixel of the CCD 9 (step SF2), and the acquired electrical signals are sent to the image-information constructing unit 137 via the signal reading unit 33. In the image-information constructing unit 137, fluorescence image information is constructed on the basis of the received electrical signals, and a process of averaging fluorescence image information of the past N0 iterations is performed (step SF3). By performing a process of averaging fluorescence image information constructed a large number of times, it is possible to reduce the level of noise randomly included in the fluorescence image information, while maintaining the luminance levels of pixels where fluorescence exists. That is, it is possible to distinguish pixels where fluorescence exists among all the pixels, so that it is possible to facilitate detection of fluorescence.

Then, if it is determined by the control unit 155 that there exists no pixel exceeding the predetermined threshold S1 ("NO" in step SF4), the procedure returns to step SF2, and the operation of steps SF2 to SF4 is repeated until a pixel exceeding the threshold S1 is found.

On the other hand, if it is determined that there exists a pixel exceeding the threshold S1 ("YES" in step SF4), the control unit 155 sets a number of iterations N1 for averaging, which represents a number of construction iterations less than the number of iterations N0 for averaging (step SF5). Then, an image of a site of the inner wall 4 of the body cavity substantially the same as the site captured in step SF2 is captured (step SF6), and the image-information constructing unit 137 performs a process of averaging fluorescence image information of the past N1 iterations among the constructed fluorescence image information (step SF7). In this case, since the number of iterations for averaging is set to N1, which is less than N0, it is possible to alleviate the effect of shaking, so that it is possible to acquire a sharper image, compared with the previous image, of the vicinity of the site where fluorescence exists.

The fluorescence image information subjected to the averaging process and having pixels with luminance levels greater than or equal to a predetermined level is sent to the memory 43 and is stored in association with time measured by the timer 41 (step SF8). By performing the process of averaging fluorescence image information as described above, it is possible to efficiently acquire fluorescence image information including regions with high fluorescence luminance levels.

In this modification, the control unit 155 performs switching from the number of iterations N0 for averaging to the number of iterations N1 for averaging. Alternatively, for example, the averaging process may be disabled when it is determined that there exists a pixel exceeding the luminance level of the predetermined threshold S1 with the number of iterations N0 for averaging, and fluorescence image information constructed most recently by the image-information constructing unit 137 may be stored in the memory 43.

Furthermore, although the image-information constructing unit 137 performs the process of averaging fluorescence image information in this modification, alternatively, a process of simply adding fluorescence image information may be performed, and the presence or absence of fluorescence may be detected on the basis of a predetermined threshold that is set correspondingly.

[Third Embodiment]

Figure 15:
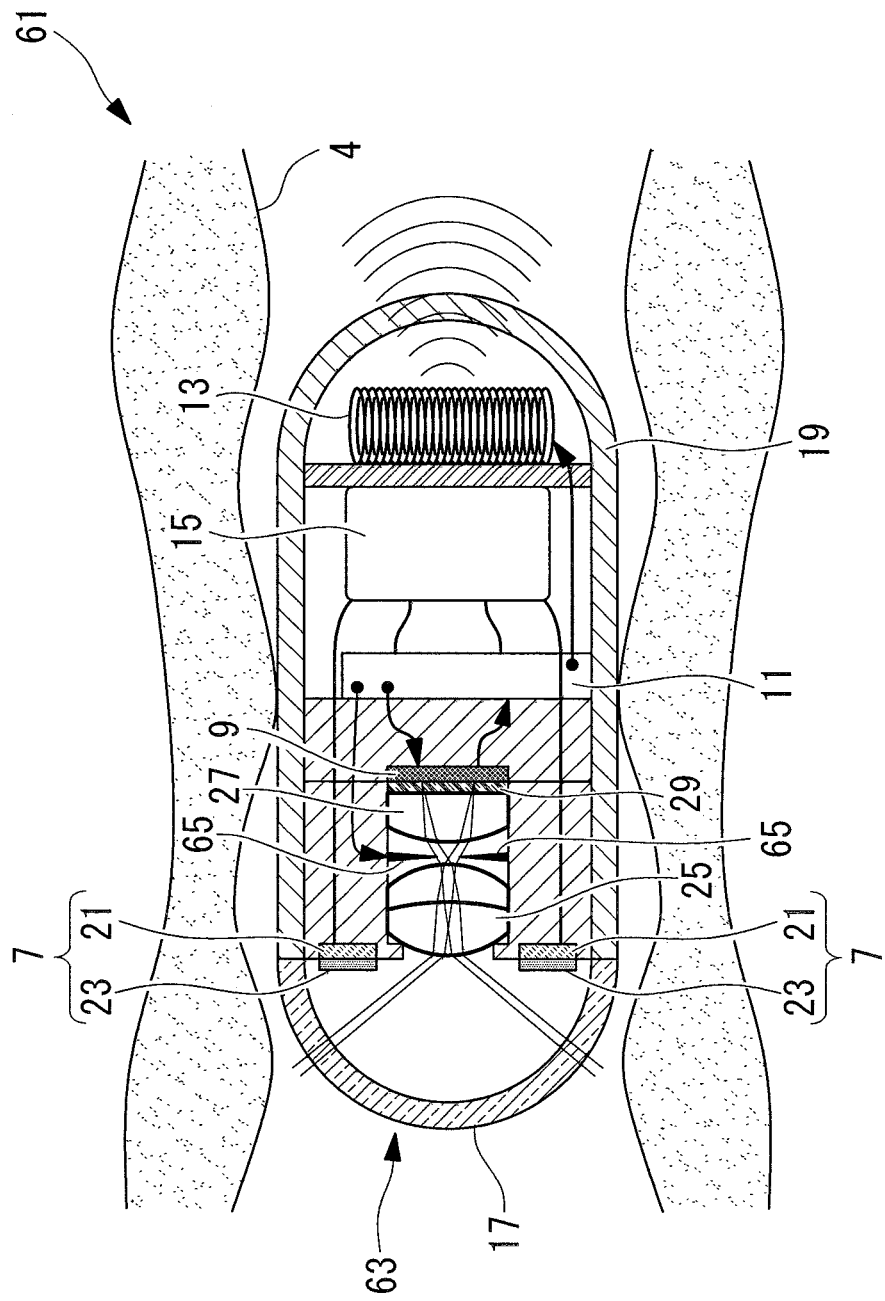
FIG. 15 is a schematic diagram showing a capsule medical system according to a third embodiment of the present invention.
Figure 16:
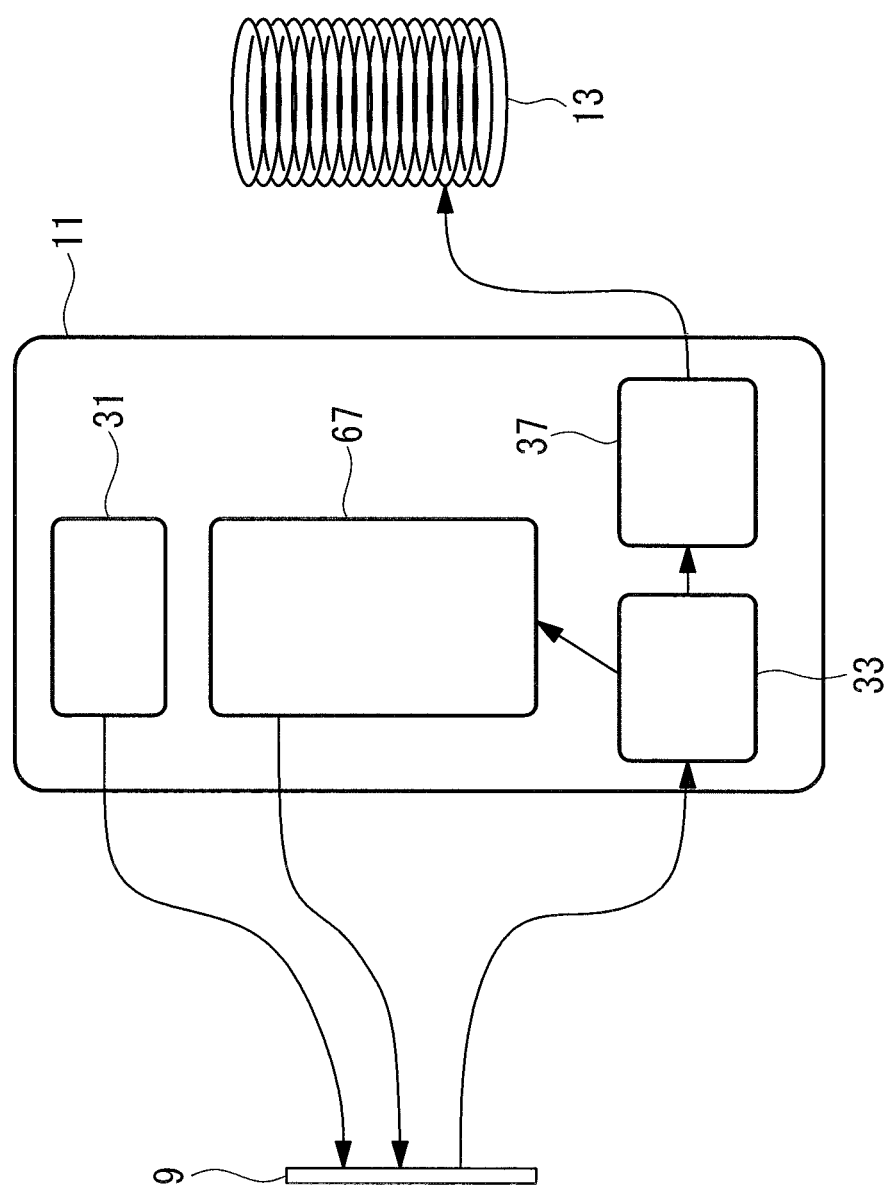
FIG. 16 is a schematic diagram showing a control device and a transmitting antenna of the capsule medical system in FIG. 15.
Figure 17:
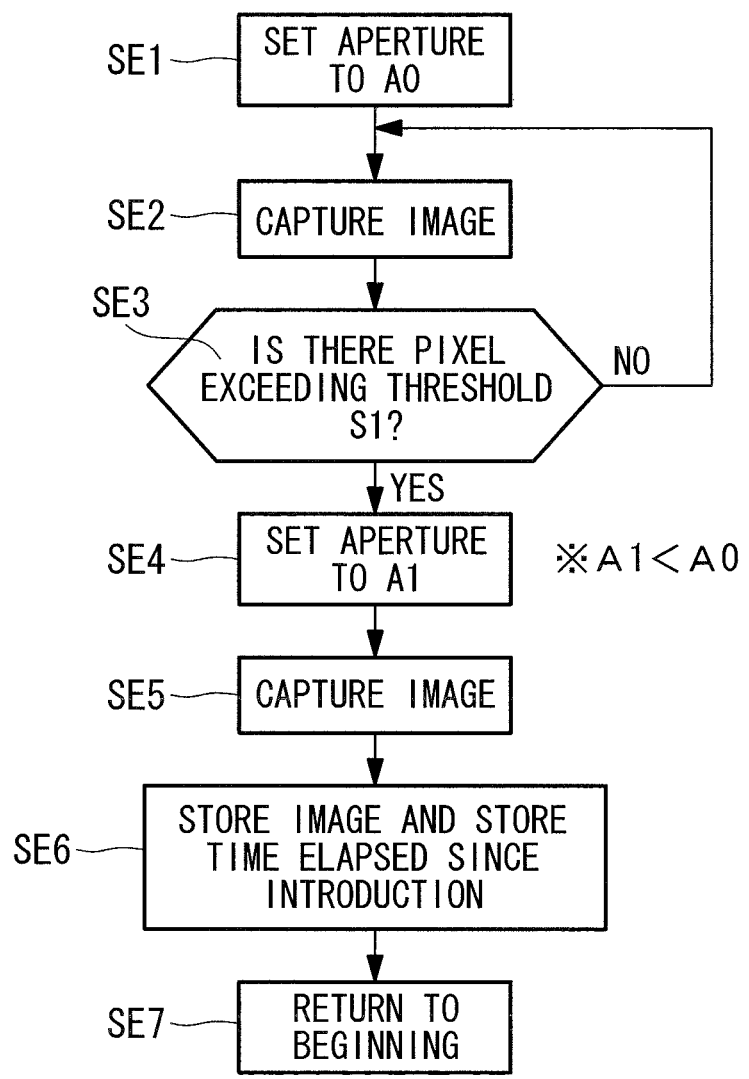
FIG. 17 is a flowchart showing the operation of the capsule medical system in FIG. 15.

Next, a capsule medical system 61 according to a third embodiment of the present invention will be described with reference to FIGS. 15 to 17.

The capsule medical system 61 according to this embodiment differs from the first embodiment in that a capsule medical device 63 includes a diaphragm 65 for adjusting the amount of fluorescence that enters the CCD 9 and in that a control unit 67 controls the size of the aperture of the diaphragm 65 instead of controlling the binning setting in the first embodiment.

In the following description of this embodiment, parts configured the same as those of the capsule medical system 1 according to the first embodiment will be designated by the same reference signs, and descriptions thereof will be omitted.

The diaphragm 65 is formed by combining thin, blade-shaped plate parts. The diaphragm 65 is disposed between the light collecting lens 25 and the image forming lens 27, and is provided so that it is possible to change the size of the aperture through which light transmitting through the light collecting lens 25 passes. Thus, the amount of fluorescence that passes through the aperture of the diaphragm 65 and enters the CCD 9 via the image forming lens 27 and the excitation-light cutting filter 29 is adjusted.

The control unit 67 is configured to perform switching of the aperture of the diaphragm 65 between an aperture A1 having such a size that an appropriate amount of light passes therethrough and an aperture A0 that is larger than the aperture A1. Furthermore, the control unit 67 is configured to control the signal reading unit 33 so that electrical signals that have been read are output to the image-information constructing unit 37 when the diaphragm 65 is set to the aperture A1.

In this embodiment, the exposure time is set to be fixed.

First, as the initial setting of the capsule medical device 63, the diaphragm 65 is set to the aperture A0 (step SE1). Upon introduction of the capsule medical device 63 in the body of the patient 2, an image is captured by detecting fluorescence at each pixel of the CCD 9 (step SE2). In this case, since the diaphragm 65 is set to the aperture A0, the range where light passes is large, so that it is possible to increase the amount of light captured at each pixel compared with the appropriate amount at the expense of the depth of field. Therefore, even with weak fluorescence, the electrical signal acquired at each pixel becomes relatively intense, so that it is possible to readily detect the presence or absence of fluorescence without fail.

Then, if it is determined by the operation of the control unit 67 that there exists no pixel exceeding the predetermined threshold S1, the procedure returns to step SE2 ("NO" in step SE3), and the operation of steps SE2 and SE3 is repeated until a pixel exceeding the threshold S1 is found.

On the other hand, if it is determined that there exists a pixel exceeding the threshold S1 ("YES" in step SE3), the control unit 67 sets the diaphragm 65 to the aperture A1 (step SE4). Then, with the diaphragm 65 set to the aperture A1, an image of a site of the inner wall 4 of the body cavity substantially the same as the site captured in step SE2 is captured (step SE5). In this case, since the aperture of the diaphragm 65 is set to the aperture A1 having such a size that an appropriate amount of light passes therethrough, it is possible to capture an image with a large depth of field, so that it is possible to acquire a sharp image, compared with the previous image, of the vicinity of the site where fluorescence exists.

At the extracorporeal device 5, fluorescence image information constructed on the basis of the electrical signals acquired by the CCD 9 through the diaphragm 65 set to the aperture A1 is stored in the memory 43 in association with time measured by the timer 41 (step SE6). After the image capturing is performed with the aperture of the diaphragm 65 set to the aperture A1, by the operation of the control unit 67, the procedure returns to step SE1 (step SE7), and the operation of steps SE1 to SE7 is repeated until the capsule medical device 63 is evacuated from the body of the patient 2.

As described above, with the capsule medical system 61 according to this embodiment, images are captured while controlling the size of the aperture of the diaphragm 65. Thus, it is possible to reduce the possibility of failure to detect a diseased region, and it is also possible to capture a sharp image representing the shape and size of the diseased region, as well as the presence or absence thereof. Furthermore, since an acquired image is associated with elapsed time, it is possible to detect the location of a diseased region. Furthermore, since only images captured with a large depth of field are transmitted, it is possible to avoid consumption of electrical power for needless transmission of fluorescence image information. Furthermore, since only images having regions with high luminance levels are saved, it is possible to save the labor of checking a huge number of images including images not having regions with high luminance levels. Accordingly, it becomes possible to observe diseased regions efficiently and in detail.

Although the embodiments of the present invention have been described above in detail with reference to the drawings, specific configurations are not limited to the embodiments, and design modifications or the like that do not depart from the spirit of the present invention are encompassed.

For example, although the CCD 9 is employed in the capsule medical systems 1, 51, and 61, alternatively, two-dimensional image capturing means, such as a CMOS device, may be employed.

Furthermore, although the embodiments have been described using fluorescence as an example of radiation, for example, light emitted from a light emitting element, Raman scattered light, reflected light, or the like may be captured.

Furthermore, without limitation to application of the present invention to the embodiments described above, the present invention may be applied to embodiments based on suitable combinations of the embodiments without particular limitation.

The invention claimed is:

1. A capsule medical device comprising:
an excitation light source that generates excitation light for irradiating an inner wall of a body cavity;
an image-capturing sensor that captures radiation generated at the inner wall of the body cavity by the excitation light emitted from the excitation light source to acquire a two-dimensional radiation image, the image-capturing sensor having variable sensitivity; and
a controller that determines whether a radiation intensity in at least part of the radiation image acquired by the image-capturing sensor exceeds a predetermined threshold and to control the image-capturing sensor so as to vary the sensitivity and resolution of the image-capturing sensor,
wherein the controller sets the sensitivity of the image-capturing sensor to a predetermined sensitivity as an initial setting,
wherein, when the radiation intensity of the radiation image acquired by the image-capturing sensor with the initial setting exceeds the predetermined threshold, the controller disables the initial setting and performs control so as to increase the resolution of the image-capturing sensor by setting the sensitivity of the image-capturing sensor lower than the predetermined sensitivity, and
wherein the controller controls the image-capturing sensor to re-acquire the radiation image with the initial setting disabled.

2. A capsule medical device according to claim 1, wherein the controller reduces the number of pixels processed together by binning of the image-capturing sensor when the radiation intensity in at least part of the radiation image acquired by the image-capturing sensor exceeds the predetermined threshold.

3. A capsule medical device according to claim 1, wherein the controller reduces the exposure time of the image-capturing sensor when the radiation intensity in at least part of the radiation image acquired by the image-capturing sensor exceeds the predetermined threshold.

4. A capsule medical device according to claim 1, further comprising a diaphragm having an aperture whose size is variable to adjust the amount of radiation that enters the image-capturing sensor,
wherein the controller reduces the size of the aperture when the radiation intensity in at least part of the radiation image acquired by the image-capturing sensor exceeds the predetermined threshold.

5. A capsule medical device according to claim 1, wherein the radiation is fluorescence generated at the inner wall of the body cavity.

6. A capsule medical device according to claim 1, wherein the radiation is Raman scattered light generated at the inner wall of the body cavity.

7. A capsule medical system comprising:
a capsule medical device according to any one of claims 1 to 6; and
an extracorporeal device disposed outside the body of a patient,
wherein the capsule medical device includes a transmitter for transmitting image signals of an image acquired by the image-capturing sensor to the outside, and
wherein the extracorporeal device includes:
a receiver for receiving the image signals from the transmitter;
a timer that measures time; and
a memory for storing the image signals received by the receiver, in association with the time measured by the timer.

8. A capsule medical device comprising:
an excitation light source that generates excitation light for irradiating an inner wall of a body cavity;
an image-capturing sensor that captures radiation generated at the inner wall of the body cavity by the excitation light emitted from the excitation light source to acquire a two-dimensional radiation image, the image-capturing sensor having variable sensitivity; and
a controller configured to control the image-capturing sensor to:
acquire the radiation image,
determine a radiation intensity of the radiation image,
reduce the sensitivity of the image-capturing sensor and increase a resolution of the image-capturing sensor when the determined radiation intensity in at least part of the radiation image acquired by the image-capturing sensor exceeds a predetermined threshold,
set the sensitivity of the image-capturing sensor to a predetermined sensitivity as an initial setting,
disable the initial setting and performs control so as to increase the resolution of the image-capturing sensor by setting the sensitivity of the image-capturing sensor lower than the predetermined sensitivity when the radiation intensity of the radiation image acquired by the image-capturing sensor with the initial setting exceeds the predetermined threshold, and
control the image-capturing sensor to re-acquire the radiation image with the initial setting disabled.

* * * * *